United States Patent [19]

Düsterlerg et al.

[11] Patent Number: 4,780,460
[45] Date of Patent: Oct. 25, 1988

[54] GLYCOESTERS OF ESTRADIOL AND ESTRIOL

[75] Inventors: Bernd Düsterlerg; Bernard Acksteiner; Paul-Eberhard Schulze, all of Berlin, Fed. Rep. of Germany

[73] Assignee: Schering Aktiengesellschaft, Berlin and Bergkamen, Fed. Rep. of Germany

[21] Appl. No.: 845,102

[22] Filed: Mar. 27, 1986

[30] Foreign Application Priority Data

Mar. 27, 1985 [DE] Fed. Rep. of Germany ....... 3511587

[51] Int. Cl.$^4$ .......................... A61K 31/56; C07J 1/00
[52] U.S. Cl. .................... 514/170; 514/182; 260/397.5
[58] Field of Search ................ 260/397.5; 514/170, 514/182

[56] References Cited

U.S. PATENT DOCUMENTS 4,260,736 4/1981 Asano et al. .................. 424/177
4,681,875 7/1987 Laurent et al. .................. 514/182

FOREIGN PATENT DOCUMENTS 2028336 3/1980 United Kingdom .

*Primary Examiner*—Leonard Schenkman
*Assistant Examiner*—Joseph A. Lipovsky
*Attorney, Agent, or Firm*—Millen & White

[57] ABSTRACT

Glycoesters of estradiol ($E_2$) and of estriol ($E_3$) of Formula I $$(E_{2,3})-O-CO-CH_2-Z \quad (I)$$

wherein

Z is hydroxy or the group —O—CO—R wherein R is methyl or phenyl, provide a uniform and enduring estrogen level especially when used in the form of an aqueous crystalline suspension.

21 Claims, No Drawings

GLYCOESTERS OF ESTRADIOL AND ESTRIOL

CROSS-REFERENCE TO RELATED APPLICATION

This application is related to U.S. Ser. No. 844,642, filed on Mrch 27, 1986, which disclosure is incorporated by reference herein.

BACKGROUND OF THE INVENTION

This invention relates to glycoesters of estradiol and estriol, processes for their preparation, and aqueous crystalline suspensions of these esters.

The natural estrogenic hormones estradiol and estriol have the disadvantage when used for medical purposes of poor solubility and rapid metabolization.

Esterification of the natural estrogens with longer-chain carboxylic acids yields estrogenically active agents that can be administered as oily solutions and exhibit long-term activity.

For example, estradiol 17-valerate, 17-enanthate, 17-undecylate, 17-cipionate, and 3-benzoate are utilized in the form of oily solutions; furthermore, use is made in medicine of a water-soluble succinic ester of estriol, namely, sodium estriol 16,17-dihemisuccinate.

Thus far, aqueous crystalline suspensions of estradiol esters and estriol esters have not been known.

SUMMARY OF THE INVENTION

It is an object of this invention to overcome or ameliorate such disadvantages.

Upon further study of the specification and appended claims, further objects and advantages of this invention will become apparent to those skilled in the art.

These objects have been achieved by providing:
glycoesters of estradiol ($E_2$) and estriol ($E_3$) of Formula I

$$(E_{2,3})-O-CO-CH_2-Z \qquad (I)$$

wherein
Z is hydroxy or the group —O—CO—R, wherein R is methyl or phenyl; e.g.,
monoglycoesters of estradiol in the 17-position; e.g.,
estradiol 17β-acetoxyacetate,
estradiol 17β-benzoyloxyacetate,
estradiol 17β-glycolate,
diglycoesters of estradiol, e.g.,
estradiol 3,17β-diacetoxyacetate,
estradiol 3,17β-dibenzoyloxyacetate,
diglycoesters of estriol in the 16,17-position, e.g.,
estriol 16α,17β-diacetoxyacetate,
estriol 16α,17β-dibenzoyloxyacetate,
triglycoesters of estriol, e.g.,
estriol 3,16α,17β-triacetoxyacetate,
estriol 3,16α,17β-tribenzoyloxyacetate, etc.

They have also been achieved in another aspect by providing aqueous crystalline suspensions of glycoesters of estradiol ($E_2$) and estriol ($E_3$), characterized by containing a compound of Formula I

$$(E_{2,3})-O-CO-CH_2-Z \qquad (I)$$

wherein
Z is hydroxy or the group —O—CO—R, wherein R is methyl or phenyl in the following fractions:
0–30% by weight of a particle size of 3–10 μm,
40–90% by weight of a particle size of 10–30 μm, and
10–30% by weight of a particle size of 25–50 μm.

In another aspect, they have been achieved by providing a process for the preparation of glycoesters of estradiol ($E_2$) and estriol ($E_3$) of Formula I

$$(E_{2,3})-O-CO-CH_2-Z \qquad (I)$$

wherein
Z is hydroxy or —O—CO—R, wherein R is methyl or phenyl,
by conventionally esterifying estradiol or estriol with an acid Z—CH$_2$—COOH or a derivative of the acid, and optionally partially saponifying the estradiol diester or the estriol triester in the 3-position.

DETAILED DISCUSSION

It has now been found that the novel glycoesters of estradiol and of estriol according to Formula I represent crystallizable compounds suitable for the preparation of microcrystalline suspensions.

It has furthermore been discovered that, for example, a crystalline suspension of 0.5 mg of estradiol 17-glycobenzoate with a percentage distribution of crystal sizes of about
15% by weight of a size of 3–10 μm,
60% by weight of a size of 10–26 μm, and
25% by weight of a size of 26–40 μm,
after a one-time intramuscular injection administered to baboons, yields an estradiol level in the plasma which lasts for 4 weeks, is adequately high, and has an extensively uniform curve.

Estradiol levels of such uniformity and such long duration cannot be achieved with the conventional estradiol esters exhibiting a lower lipophilicity.

The galenic formulation of the novel esters as a crystalline suspension furthermore offers the advantage that these esters, together with corresponding esters of norethisterone or the steroids derived from norethisterone, e.g, levonorgestrel, gestodene, desogestrel, and lynestrenol, can be utilized as contraceptives in an aqueous crystalline suspension. For example, 10–50 mg of steroid glycoester of the norethisterone type and 0.5–10 mg of steroid glycoester of the estradiol or estriol type can be made available in the form of an aqueous crystalline suspension as a one-month injection for contraception. See U.S. Ser. No. 844,642, filed Mar. 27, 1986, above. Crystalline particle distributions useful for preparing particle size fractions useful in conjunction with this invention can be prepared fully conventionally by granulating, crushing, grinding, etc., e.g., using mechanical or other conventional methods, especially ultrasonic treatment, followed by fully conventional screening. Such procedures are well known and described, e.g., in Remington's Pharmaceutical Sciences, 15th Edition 1975, Page 322, Mack Publishing Company, Easton, Pa.

A microcrystalline suspension of a glycoester of estradiol or estriol of formula I can be prepared according to conventional methods and screened so that three fractions are obtained having the following particle sizes:
(a) 3–10 μm,
(b) 10–30 μm, and
(c) 25–50 μm.
0–30% by weight of (a)
40–90% by weight of (b), and
10–30% by weight of (c)

are mixed in a fluidized bed for about 5 minutes, filled up with a physiological sodium chloride solution, optionally with addition of a stabilizer, such as polyoxyethylene stearate ("Myrj"), and heat-sterilized, or dispensed aseptically.

Within each range, the particle distribution is approximately flat, but is not critical.

Esterification can be effected conventionally by reaction of estradiol or estriol with the acid Z—CH$_2$—COOH or a derivative of the acid in the presence of a base. Especially suitable as the acid derivative is the chloride and as the base, in particular, pyridine, dimethylamino-pyridine, or collidine. If esters are desired having a free 3-hydroxy group, the 3-ester can be partially saponified with an inorganic base, e.g., with potassium carbonate in water and methanol.

The foregoing weight percentages are based on total weight of steroid. The concentration of steroid of Formula I in the aqueous suspension is usually in the range of 1–20 mg/ml. Other optional ingredients in such suspensions can be included also. Such ingredients are, for instance, methyl cellulose and hydroxypropyl cellulose.

The suspensions and compounds of this invention can be used as a contraceptive component in female mammals, including humans, e.g., in conjunction with gestagens in accordance with fully conventional methods and considerations.

It is also possible to utilize the suspensions of this invention and the new compounds of this invention for the purposes for which estrogens per se are administered apart from their combinations with gestagens. For example, they can be used to treat postmenopausal women suffering from climacteric deficiency symptoms.

The suspensions of this invention are preferably administered by injection, preferably intramuscularly. Gestagens which can be incorporated in the suspension or which can be administered separately, simultaneously or sequentially, include all conventional gestagens which are well known to those skilled in the art. In an especially preferred embodiment, the gestagen will be a long-acting gestagen which can be co-administered with the suspension of this invention over an a long time interval, e.g., preferably only once a month. Such gestagens preferably are those of U.S. Ser. No. 844,642, filed Mar. 27, 1986, discussed above. Generally, the administration of the contraceptive preparations of this invention is analogous to Depo-Clinovir ®.

The one-month single dose effective for contraception for human patients is 20–50 mg of the steroid or, 30–75 mg of the glycoester of the mentioned norethisterone type used in a special embodiment wherein the long-acting glycoesters of this invention are combined with similar suspensions of long-acting gestagens, especially those of U.S. Ser. No. 844,642, filed Mar. 27, 1986, discussed above. General amounts of the glycoesters of this invention are 0.5–20 mg.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the preceding text and the following examples, all temperatures are set forth uncorrected in degrees Celsius and all parts and percentages are by weight; unless otherwise indicated.

EXAMPLE 1

In an aseptic and pyrogen-free sonic treatment apparatus, 0.5 g of estradiol 17$\beta$-benzoyloxyacetate in 5 ml of "Myrj"-sodium chloride solution (0.9% by weight sodium chloride solution with 0.085% by weight "Myrj") is subjected to sonic treatment for 3 minutes, and the resultant suspension is fractionally screened. A particle size distribution is obtained of
(a) 3–10 $\mu$m,
(b) 10–26 $\mu$m, and
(c) 26–40 $\mu$m.

Fractions (a), (b), and (c) are mixed in a fluidized bed in a ratio of 15:60:25 and filled up to 100 ml with "Myrj"-sodium chloride solution.

EXAMPLE 2

Under the same conditions as set forth in Example 1, 5 g of 17$\alpha$-ethynyl-17$\beta$-(O-benzoylglycoloyloxy)-4-estren-e-one in 50 ml of "Myrj"-sodium chloride solution is subjected to sonic treatment for 30 minutes. Fractions having the following particle sizes are withdrawn:
(a) 10% by weight of a size of 5–15 $\mu$m,
(b) 50% by weight of a size of 15–50 $\mu$m, and
(c) 40% by weight of a size of 35–50 $\mu$m.

See U.S. Ser. No. 844,642, filed Mar. 27, 1986, above.

Fractions (a), (b), and (c) according to Example 1 are suspended with (a), (b), and (c) according to Example 2 in 100 ml of "Myrj"-sodium chloride solution and dispensed under aseptic and sterile conditions into injection kits of respectively 1 ml content.

EXAMPLE 3

Estradiol 3,17$\beta$-Diacetoxyacetate

Under nitrogen, 3 g (21.9 mmol) of acetoxyacetyl chloride in 10 ml of tetrachloroethylene is added dropwise at 120° C. within 2 hours to a solution of 1.24 g (4.5 mmol) of estradiol in 7.5 ml of collidine and 7.5 ml of tetrachloroethylene under agitation. The cooled solution is added to 5 g of oxalic acid in 20 ml of water and the mixture is stirred for another 20 minutes. The mixture is diluted with methylene chloride, and the organic phase is extracted by shaking with sodium bicarbonate solution and water and dried over sodium sulfate. The residue is subjected to low-pressure chromatography on silica gel, mobile phase methylene chloride/methylene chloride-acetone (1–2%), thus obtaining 1.23 g of estradiol 3,17$\beta$-diacetoxyacetate, mp 95° C.

EXAMPLE 4

Estradiol 17$\beta$-Acetoxyacetate

A solution is prepared from 0.9 g of estradiol 3,17$\beta$-diacetoxyacetate in 10 ml of acetone; 5 ml of potassium carbonate solution (250 mg of potassium carbonate in 5 ml of water and 45 ml of methanol) is added thereto, and the mixture is stirred for 10 minutes. Then the mixture is acidified and methanol and acetone distilled off under vacuum. The residue is taken up in 10 ml of methylene chloride, washed with sodium bicarbonate solution and water, dried over sodium sulfate, and evaporated. The residue is subjected to low-pressure chromatography on silica gel, mobile phase methylene chloride/methylene chloride-acetone (0.5–1%), thus obtaining 0.28 g of estradiol 17$\beta$-acetoxyacetate, mp 170°–172° C.

As a by-product of the saponification with potassium carbonate according to Example 4, estradiol 17β-glycolate is obtained, mp 231°–236° C.

EXAMPLE 5

Estradiol 3,17β-Dibenzoyloxyacetate

Under nitrogen, at a bath temperature of 120° C., 2 g (10 mmol) of benzoyloxyacetyl chloride is added dropwise within 2 hours to a solution of 1.36 g (5 mmol) of estradiol in 7.5 ml of collidine and 7.5 ml of tetrachloroethylene. Then the cooled solution is poured to 5 g of oxalic acid in 20 ml of water and stirred for 20 minutes. The organic phase is extracted by shaking with sodium bicarbonate solution and water and dried over sodium sulfate. The residue is subjected to low-pressure chromatography on silica gel, mobile phase methylene chloride, yielding 1.79 g of estradiol 3,17β-dibenzoyloxyacetate, mp 105° C.

Benzoyloxyacetyl chloride is obtained by reacting benzoylacetoxyacetic acid with oxalyl chloride.

EXAMPLE 6

Estradiol 17β-Benzoyloxyacetate 1.79 g of estradiol 3,17β-dibenzoyloxyacetate is dissolved in 32 ml of acetone and, after adding 10 ml of a potassium carbonate solution (250 mg of potassium carbonate in 5 ml of water and 45 ml of methanol), agitated for 10 minutes. The mixture is then acidified, and methanol and acetone are distilled off under vacuum. The organic residue is taken up in 10 ml of methylene chloride, washed with sodium bicarbonate and water, and dried over sodium sulfate. The residue is subjected to low-pressure chromatography on silica gel, mobile phase methylene chloride/methylene chloride-acetone up to 1%, thus obtaining 0.79 g of estradiol 17β-benzoyloxyacetate, mp 153°–155° C.

EXAMPLE 7

Estriol 3,16α,17β-Triacetoxyacetate

Under nitrogen, at a bath temperature of 120° C., 5 g (37 mmol) of acetoxyacetyl chloride is added dropwise within 2 hours to a solution of 1.45 g (5 mmol) of estriol in 20 ml of tetrachloroethylene and 7.5 ml of collidine. Then the cooled solution is poured to 5 g of oxalic acid in 20 ml of water and stirred for 20 minutes. The organic phase is extracted by shaking with sodium bicarbonate solution and water and dried over sodium sulfate. The residue is subjected to low-pressure chromatography on silica gel, mobile phase methylene chloride, yielding 1.15 g of estriol 3,16α,17β-triacetoxyacetate, mp 70° C.

EXAMPLE 8

Estriol 16α,17β-Diacetoxyacetate 1.15 g of estriol 3,16α,17β-triacetoxyacetate is dissolved in 5 ml of acetone; 5 ml of potassium carbonate solution (250 mg of potassium carbonate in 5 ml of water and 45 ml of methanol) is added thereto and the mixture is stirred for 10 minutes. Then the mixture is acidified and the solvent removed by distillation. The residue is taken up in 10 ml of methylene chloride, washed with sodium bicarbonate solution and water, and dried over sodium sulfate and evaporated. The residue is subjected to low-pressure chromatography on silica gel, mobile phase methylene chloride/methylene chloride-acetone, 0.5–1%, thus obtaining 0.52 g of estriol 16α,17β-diacetoxyacetate, mp 170° C.

EXAMPLE 9

Estriol 3,16α,17β-Tribenzoyloxyacetate

Under nitrogen, at a bath temperature of 120° C., a solution of 2 g (10 mmol) of benzoyloxyacetyl chloride in 10 ml of tetrachloroethylene is added dropwise within 2 hours to a solution of 0.95 g (3.3 mmol) of estriol in 7.5 ml of tetrachloroethylene and 7.5 ml of collidine. The cooled solution is then poured to 5 g of oxalic acid in 20 ml of water and stirred for 20 minutes. The organic phase is extracted by shaking with sodium bicarbonate solution and water and dried over sodium sulfate. The residue is subjected to low-pressure chromatography on silica gel, mobile phase methylene chloride/methylene chloride-acetone (0.5–2%), thus obtaining 1.36 g of estriol 3,16α,17β-tribenzoyloxyacetate, mp 95° C.

EXAMPLE 10

Estriol 16α,17β-Dibenzoyloxyacetate 1.36 g of estriol 3,16α,17β-tribenzoyloxyacetate is dissolved in 7 ml of acetone; 6 ml of potassium carbonate solution (125 mg of potassium carbonate in 5 ml of water and 45 ml of methanol) is added thereto and the mixture agitated for 10 minutes. Thereafter the mixture is acidified and the solvent removed by distillation. The residue is taken up in 10 ml of methylene chloride, washed with sodium bicarbonate solution and water, and dried over sodium sulfate and evaporated. The residue is subjected to low-pressure chromatography on silica gel, mobile phase methylene chloride/methylene chloride-acetone to 1%, thus obtaining 0.56 g of estriol 16α,17β-dibenzoyloxyacetate, mp 160° C.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A glycoester of estradiol ($E_2$) or estriol ($E_3$) of the formula $$(E_{2,3})-O-CO-CH_2-Z$$

wherein

Z is —O—CO—R wherein R is methyl or phenyl.

2. A glycoester of $E_2$ of claim 1.

3. A glycoester of claim 2, wherein Z is —O—CO—CH$_3$.

4. A glycoester of claim 2, wherein Z is —O—CO—phenyl.

5. A glycoester of $E_3$ of claim 1.

6. A glycoester of claim 5, wherein Z is —O—CO—CH$_3$.

7. A glycoester of claim 5, wherein Z is —O—CO—phenyl.

8. A monoglycoester of estradiol in the 17-position which is
estradiol 17β-acetoxyacetate,
estradiol 17β-benzoyloxyacetate, or estradiol 17β-glycolate, each a compound of claim 1.

9. A diglycoester of estradiol which is
estradiol 3,17β-diacetoxyacetate, or
estradiol 3,17β-dibenzoyloxyacetate, each a compound of claim 1.

10. A diglycoester of estriol in the 16,17-position which is
estriol 16α,17β-diacetoxyacetate, or
estriol 16α,17β-dibenzoyloxyacetate, each a compound of claim 1.

11. A triglycoester of estriol which is
estriol 3,16α,17β-triacetoxyacetate,
estriol 3,16α,17β-tribenzoyloxyacetate, each a compound of claim 1.

12. An aqueous crystalline suspension comprising a glycoester of estradiol ($E_2$) or estriol ($E_3$), of claim 1, in the following fractions:
0-30% by weight of a particle size of 3-10 μm,
40-90% by weight of a particle size of 10-26 μm,
10-30% by weight of a particle size of 26-40 μm.

13. A suspension of claim 12 wherein the glycoester is
estradiol 17β-acetoxyacetate,
estradiol 17β-benzoyloxyacetate,
estradiol 17β-glycolate,
estradiol 3,17β-diacetoxyacetate,
estradiol 3,17β-dibenzoyloxyacetate,
estriol 16α,17β-diacetoxyacetate,
estriol 16α,17β-dibenzoyloxyacetate,
estriol 3,16α,17β-triacetoxyacetate, or
estriol 3,16α,17β-tribenzoyloxyacetate.

14. A suspension of claim 13, wherein the amount of glycoester is 0.5-10 mg.

15. A suspension of claim 12, further comprising an amount of a gestagen effective as a contraceptive.

16. A suspension of claim 15, wherein the gestagen is a long-acting gestagen.

17. A method of achieving a depot effect of a glycoester of estradiol ($E_2$) or estriol ($E_3$) of the formula $$(E_{2,3})-O-CO-CH_2-Z$$

wherein
Z is hydroxy or —O—CO—R wherein R is methyl or phenyl, comprising administering an effective amount of the glycoester to a patient as an aqueous suspension of claim 1.

18. A method of claim 17, wherein the effect is contraception in a female and further comprising administering an amount of a gestagen effective as a contraceptive.

19. A method of claim 18, wherein the administration of the steroid of said formula is once every 4 weeks.

20. A method of claim 19, wherein the aqueous suspension further comprises a gestagen which also is administered once every 4 weeks.

21. A method of claim 19, wherein the amount of the steroid of said formula is 0.5-10 mg.

* * * * *